United States Patent [19]

Clemons

[11] Patent Number: Plant 5,485

[45] Date of Patent: Jun. 4, 1985

[54] PECAN TREE (JUBILEE)

[76] Inventor: Melvin B. Clemons, Rte. 1, Box 1315, Foley, Ala. 36535

[21] Appl. No.: 551,937

[22] Filed: Nov. 15, 1983

[51] Int. Cl.[3] ..... A01H 5/00

[52] U.S. Cl. ..... Plt./31

[58] Field of Search ..... Plt./31

*Primary Examiner*—James R. Feyrer

[57] ABSTRACT

A pecan tree designated "Jubilee," a cultivated seedling, said tree displaying particularly valuable commercial characteristics in that it annually produces a high quality crop of thin-shelled nuts without the benefit of fungicide sprays under conditions of severe pecan scab disease pressure. Early maturity of the nuts further enhances the commercial value.

3 Drawing Figures

The present invention relates to a new and distinct variety of pecan tree discovered by me on my property in Baldwin County, Ala., as a selected, cultivated seedling of unknown parentage, one of numerous seedlings (each different), growing on my property. Subject seedling will be known commercially as "Jubilee" variety.

My attention was directed and devoted to this particular seedling above all others I cultivate because it annually produced a good crop of high quality nuts, including years of complete crop failure on adjacent improved varieties.

Continued tests, observations and research over a prolonged period of years have convinced me that my "Jubilee" seedling is a distinct new variety which is distinguished from all other pecan varieties of which I am aware, as evidenced by the following unique combination of commercially valuable features which are outstanding in the "Jubilee":

(1) A distinctive and attractive appearance and shape of the nut and the kernel;

(2) Consistently good annual productivity of large nuts of excellent quality and flavor, said nuts having medium thin shells (between Cape Fear and Stuart varieties) which separate exceptionally easily from the kernels;

(3) A self-fertile habit which assures good annual nut crops;

(4) Highly resistant to pecan scab disease as evidenced by its annual production of a good quality nut crop, without the use of fungicide, in Baldwin County, Ala., an area with annual rainfall of 66 to 72 inches;

(5) Matures medium early, thereby allowing ample time for marketing in time to meet Thanksgiving holiday demand for pecans. This feature in itself enhances the price paid to the grower.

Asexual reproduction of my new "Jubilee" pecan variety by grafting as performed by me in Baldwin County, Ala., shows that the foregoing characteristics and distinctions come true and are established and transmitted through succeeding propagations.

The accompanying photographic drawings show typical specimens of the foliage, nuts, and growth pattern of my new "Jubilee" pecan variety. Shells of some of the nut specimens are removed to display the kernels. All specimens are depicted as nearly true in shape and/or size and color as is reasonably possible.

The following is a detailed description of my new variety, with color terminology in accordance with Maerz and Paul's, A Dictionary of Color, First Edition, as based on observations of specimens grown and observed in Baldwin County, Ala.

Parentage: A selected cultivated seedling of unknown parentage.

Propagation: Holds its distinguishing characteristics through succeeding propagation by grafting.

Dates of first and last pickings: September 30 and October 10, respectively, in Baldwin County, Ala.

Maturity season: Early mid-season, late September to early October in Baldwin County, Ala.

Tree: Large, vigorous, consistently good productivity annually.

- *Growth habit.*—Vigorous, upright, modified central leader.
- *Wood (second year).*—Color — Cub, Plate 15, C2, page 53.
- *Foliage.*—Abundant, large, heavy.
- *Buds.*—Medium-long, pointed.

Nuts:

- *Ripening.*—Even; Time of harvesting — from about September 30 to October 10.
- *Quantity.*—Abundant.
- *Maturity.*—Medium early.
- *Tenacity.*—Free.
- *Cluster.*—Average number of nuts to cluster, 3 or 4; Size — large.
- *Size.*—Length, about 21/16 inches; Diameter, about 1 inch.
- *Weight.*—Average number of nuts to pound, from 42 to 47.
- *Shape.*—Base, tapered with short point; Point, medium-sharp with distinctive curvature.
- *Shell.*—Medium thin; cracks and releases easily. Color — Arizona, Plate 13, E6, page 49.
- *Kernel.*—Flavor, good; Shape, elongated oval; Texture, very firm; Sutures, uneven, spreading at basal end.

I claim:

1. A new and distinct variety of pecan tree, substantially as herein shown and described, characterized particularly as to novelty by the unique combination of medium-early maturity of high quality, large nuts on an annual basis, without the use of fungicide in an area where most pecan varieties are severely affected by pecan scab disease, said nuts having medium-thin shells which separate easily from the kernel, and a self-fertile habit which assures good annual nut crops even in the absence of any neighboring pecan trees.

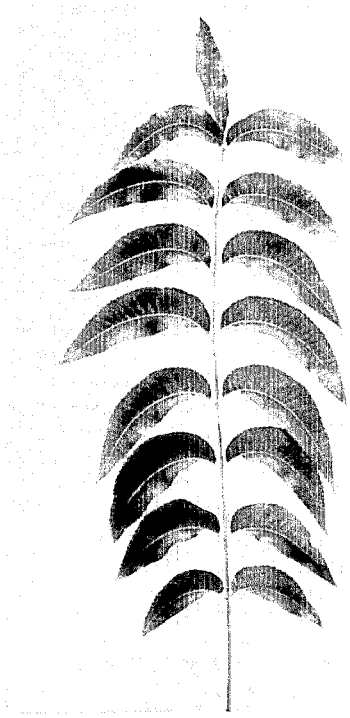
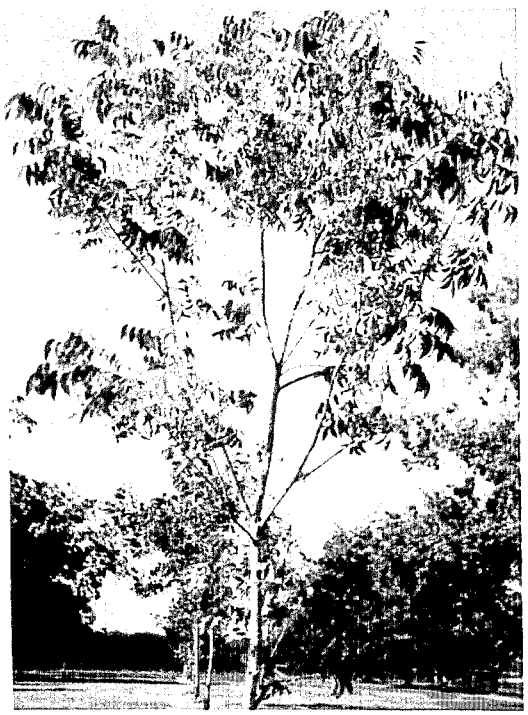
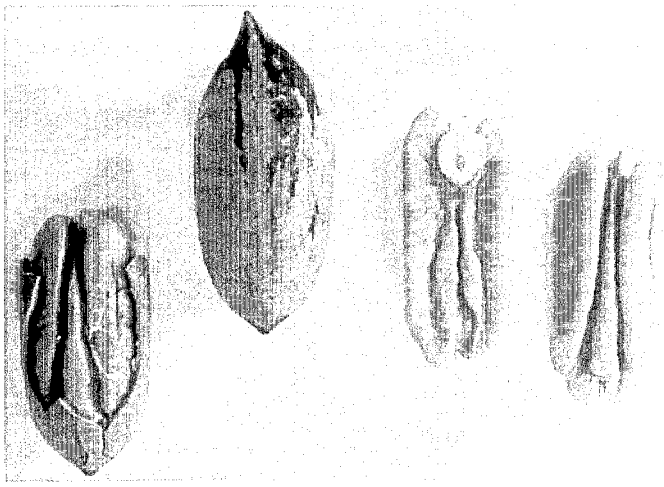

* * * * *